United States Patent [19]

Burnham et al.

[11] Patent Number: 5,955,078
[45] Date of Patent: Sep. 21, 1999

[54] FIBRONECTIN BINDING PROTEIN POLYPEPTIDES

[75] Inventors: Martin Karl Russel Burnham, Horsham; Ian Chopra, Guildford; Ian Alfred Critchley, Crawley; David Justin Charles Knowles, Reigate, all of United Kingdom

[73] Assignee: Smithkline Beecham p.l.c., Brentford, United Kingdom

[21] Appl. No.: 08/459,135

[22] Filed: Jun. 2, 1995

Related U.S. Application Data

[63] Continuation of application No. PCT/GB94/00215, Feb. 4, 1994.

[30] Foreign Application Priority Data

Feb. 5, 1993 [GB] United Kingdom .................... 9302289
Oct. 20, 1993 [GB] United Kingdom .................... 9321592

[51] Int. Cl.$^6$ ......................... A61K 39/02; A61K 39/085; A61K 38/00; C07K 1/00
[52] U.S. Cl. ..................... 424/190.1; 424/234.1; 424/243.1; 530/300; 530/350; 536/23.7
[58] Field of Search ..................... 530/300, 350; 536/23.7; 424/190.1, 234.1, 243.1

[56] References Cited

U.S. PATENT DOCUMENTS 4,578,355  3/1986  Rosenberg .
5,034,515  7/1991  Proctor .
5,440,014  8/1995  Hook et al. .

FOREIGN PATENT DOCUMENTS

WO 90/03398  4/1990  WIPO .
WO 92/02555  2/1992  WIPO .

OTHER PUBLICATIONS

Lazar et al (Molecular & Cellular Bio. vol. 8 No. 3, Mar. 1988 pp. 1247–1252).
Burgess et al (J. Of Cell Biology vol. III, No. 1990 pp. 2129–2138).
Salgaller et al (Cancer. Immunol. Immunother. 1994 vol. 39, pp. 105–116).
Flock et al (EMBO Journal vol. 6, No. 8, pp. 2351–2357 1987).
Eperse et al (Infection & Immunity vo. 37 No. 3, Aug. 1982 pp. 526–531).
Signas et al (PNAS vol. 86, Jan. 1989 pp. 699–703).
Johnson et al (Eur, J. Biochem. vol. 202, 1991 pp. 1041–1048).

*Primary Examiner*—Anthony C. Caputa
*Assistant Examiner*—Mark Navarro
*Attorney, Agent, or Firm*—Edward R. Gimmi; William T King

[57] ABSTRACT

A monoclonal antibody (Mab), or a fragment thereof, that binds to one or more epitopes of a matrix binding protein and an isolated D1–D4 polypeptide (SEQ ID NO. 6, 7, and 8) from a *Staphylococcus aureus* Fbp and their use in the prevention of adhesion of bacteria, in particular gram positive bacteria, to extracellular matrix proteins on in-dwelling devices or to matrix proteins in wounds.

6 Claims, 1 Drawing Sheet

SEQUENCE LISTING (1) GENERAL INFORMATION:

(iii) NUMBER OF SEQUENCES: 15

(2) INFORMATION FOR SEQ ID NO: 1:

(i) SEQUENCE CHARACTERISTICS:
      (A) LENGTH: 36 base pairs
      (B) TYPE: nucleic acid
      (C) STRANDEDNESS: single
      (D) TOPOLOGY: linear (ii) MOLECULE TYPE: GENOMIC DNA (xi) SEQUENCE DESCRIPTION: SEQ ID NO: 1:

```
GGGAATTCAT ATGGGCCAAA ATAGCGGTAA CCAGTC                                36
```

(2) INFORMATION FOR SEQ ID NO: 2:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: GENOMIC DNA (xi) SEQUENCE DESCRIPTION: SEQ ID NO: 2:

```
GCGGATCCTT ACGTTGGTGG CACGATTGGA GGTG                                  34
```

(2) INFORMATION FOR SEQ ID NO: 3:

(i) SEQUENCE CHARACTERISTICS:
        (A) LENGTH: 68 base pairs
        (B) TYPE: nucleic acid
        (C) STRANDEDNESS: single
        (D) TOPOLOGY: linear (ii) MOLECULE TYPE: GENOMIC DNA (xi) SEQUENCE DESCRIPTION: SEQ ID NO: 3:

```
CGGAATTCGT CAACAAACGA TTGAAGAAGA TACAACGACG TAAGATCTGG ATCCGCATGC      60

GAATTCCG                                                               68
```

(2) INFORMATION FOR SEQ ID NO: 4:

(i) SEQUENCE CHARACTERISTICS:
        (A) LENGTH: 68 base pairs
        (B) TYPE: nucleic acid
        (C) STRANDEDNESS: single
        (D) TOPOLOGY: linear (ii) MOLECULE TYPE: GENOMIC DNA (xi) SEQUENCE DESCRIPTION: SEQ ID NO: 4:

```
CGGAATTCGT CAACAAACGA TTGAAGAAGA TACAACGCCG TAAGATCTGG ATCCGCATGC      60

GAATTCCG                                                               68
```

(2) INFORMATION FOR SEQ ID NO: 5:

(i) SEQUENCE CHARACTERISTICS:
        (A) LENGTH: 546 base pairs
        (B) TYPE: nucleic acid
        (C) STRANDEDNESS: single
        (D) TOPOLOGY: linear (ii) MOLECULE TYPE: GENOMIC DNA (xi) SEQUENCE DESCRIPTION: SEQ ID NO: 5:

```
GGCCAAAATA GCGGTAACCA GTCATTCGAG GAAGACACAG AAGAAGATAA ACCTAAATAT      60

GAACAAGGTG GCAATATCGT AGATATCGAT TTCGATAGTG TACCTCAAAT TCATGGTCAA     120

AATAAAGGTG ATCAGTCATT CGAAGAAGAT ACAGAGAAAG ACAAGCCTAA ATATGAACAT     180

GGTGGTAATA TCATTGATAT CGACTTCGAC AGCGTGCCAC ATATTCATGG ATTCAATAAG     240

CACACTGAAA TTATTGAAGA AGATACAAAC AAAGATAAAC CAAATTATCA ATTCGGTGGA     300

CACAATAGTG TTGACTTTGA AGAAGATACA CTTCCACAAG TAAGTGGTCA TAATGAAGGT     360
```

```
CAACAAACGA TTGAAGAAGA TACAACGCCG CCAACACCAC CAACACCAGA AGTACCAAGT    420

GAGCCGGAAA CACCAACACC ACCGACACCA GAAGTACCAA GTGAGCCGGA AACACCAACA    480

CCGCCAACAC CAGAGGTACC AAGTGAGCCG GAAACACCAA CACCTCCAAT CGTGCCACCA    540

ACGTAA                                                              546
```

(2) INFORMATION FOR SEQ ID NO: 6:

(i) SEQUENCE CHARACTERISTICS:
        (A) LENGTH: 181 amino acids
        (B) TYPE: amino acid
        (C) STRANDEDNESS: single
        (D) TOPOLOGY: linear (ii) MOLECULE TYPE: Protein (xi) SEQUENCE DESCRIPTION: SEQ ID NO: 6:

```
Gly Gln Asn Ser Gly Asn Gln Ser Phe Glu Glu Asp Thr Glu Glu Asp
 1               5                  10                  15

Lys Pro Lys Tyr Glu Gln Gly Gly Asn Ile Val Asp Ile Asp Phe Asp
             20                  25                  30

Ser Val Pro Gln Ile His Gly Gln Asn Lys Gly Asp Gln Ser Phe Glu
         35                  40                  45

Glu Asp Thr Glu Lys Asp Lys Pro Lys Tyr Glu His Gly Gly Asn Ile
 50                  55                  60

Ile Asp Ile Asp Phe Asp Ser Val Pro His Ile His Gly Phe Asn Lys
 65                  70                  75                  80

His Thr Glu Ile Ile Glu Glu Asp Thr Asn Lys Asp Lys Pro Asn Tyr
                 85                  90                  95

Gln Phe Gly Gly His Asn Ser Val Asp Phe Glu Glu Asp Thr Leu Pro
            100                 105                 110

Gln Val Ser Gly His Asn Glu Gly Gln Gln Thr Ile Glu Glu Asp Thr
            115                 120                 125

Thr Pro Pro Thr Pro Pro Thr Pro Glu Val Pro Ser Glu Pro Glu Thr
130                 135                 140

Pro Thr Pro Pro Thr Pro Glu Val Pro Ser Glu Pro Glu Thr Pro Thr
145                 150                 155                 160

Pro Pro Thr Pro Glu Val Pro Ser Glu Pro Glu Thr Pro Thr Pro Pro
                165                 170                 175

Ile Val Pro Pro Thr
            180
```

(2) INFORMATION FOR SEQ ID NO: 7:

(i) SEQUENCE CHARACTERISTICS:
        (A) LENGTH: 130 amino acids
        (B) TYPE: amino acid
        (D) TOPOLOGY: linear (ii) MOLECULE TYPE: protein (xi) SEQUENCE DESCRIPTION: SEQ ID NO: 7:

```
Gly Gln Asn Ser Gly Asn Gln Ser Phe Glu Glu Asp Thr Glu Glu Asp
 1               5                  10                  15

Lys Pro Lys Tyr Glu Gln Gly Gly Asn Ile Val Asp Ile Asp Phe Asp
             20                  25                  30

Ser Val Pro Gln Ile His Gly Gln Asn Lys Gly Asp Gln Ser Phe Glu
         35                  40                  45

Glu Asp Thr Glu Lys Asp Lys Pro Lys Tyr Glu His Gly Gly Asn Ile
```

```
            50                  55                  60
    Ile Asp Ile Asp Phe Asp Ser Val Pro His Ile His Gly Phe Asn Lys
    65                  70                  75                  80

His Thr Glu Ile Ile Glu Glu Asp Thr Asn Lys Asp Lys Pro Asn Tyr
                        85                  90                  95

Gln Phe Gly Gly His Asn Ser Val Asp Phe Glu Glu Asp Thr Leu Pro
                    100                 105                 110

Gln Val Ser Gly His Asn Glu Gly Gln Gln Thr Ile Glu Glu Asp Thr
                115                 120                 125

Thr Thr
    130
```

(2) INFORMATION FOR SEQ ID NO: 8:

(i) SEQUENCE CHARACTERISTICS:
        (A) LENGTH: 130 amino acids
        (B) TYPE: amino acid
        (D) TOPOLOGY: linear (ii) MOLECULE TYPE: protein (xi) SEQUENCE DESCRIPTION: SEQ ID NO: 8:

```
    Gly Gln Asn Ser Gly Asn Gln Ser Phe Glu Glu Asp Thr Glu Glu Asp
    1               5                   10                  15

Lys Pro Lys Tyr Glu Gln Gly Gly Asn Ile Val Asp Ile Asp Phe Asp
                    20                  25                  30

Ser Val Pro Gln Ile His Gly Gln Asn Lys Gly Asp Gln Ser Phe Glu
                    35                  40                  45

Glu Asp Thr Glu Lys Asp Lys Pro Lys Tyr Glu His Gly Gly Asn Ile
    50                  55                  60

Ile Asp Ile Asp Phe Asp Ser Val Pro His Ile His Gly Phe Asn Lys
    65                  70                  75                  80

His Thr Glu Ile Ile Glu Glu Asp Thr Asn Lys Asp Lys Pro Asn Tyr
                        85                  90                  95

Gln Phe Gly Gly His Asn Ser Val Asp Phe Glu Glu Asp Thr Leu Pro
                    100                 105                 110

Gln Val Ser Gly His Asn Glu Gly Gln Gln Thr Ile Glu Glu Asp Thr
                115                 120                 125

Thr Pro
    130
```

(2) INFORMATION FOR SEQ ID NO: 9:

(i) SEQUENCE CHARACTERISTICS:
        (A) LENGTH: 524 base pairs
        (B) TYPE: nucleic acid
        (C) STRANDEDNESS: single
        (D) TOPOLOGY: linear (ii) MOLECULE TYPE: GENOMIC DNA (xi) SEQUENCE DESCRIPTION: SEQ ID NO: 9:

```
GGCCAAAATA GCGGTAACCA GTCATTCGAG GAAGACACAG AAGAAGATAA ACCTAAATAT    60

GAACAAGGTG GCAATATCGT AGATATCGAT TTCGATAGTG TACCTCAAAT TCATGGTCAA   120

AATAAAGGTG ATCAGTCATT CGAAGAAGAT ACAGAGAAAG ACAAGCCTAA ATATGAACAT   180

GGTGGTAATA TCATTGATAT CGACTTCGAC AGCGTGCCAC ATATTCATGG ATTCAATAAG   240

CACACTGAAA TTATTGAAGA AGATACAAAC AAAGATAAAC CAAATTATCA ATTCGGTGGA   300

CACAATAGTG TTGACTTTGA AGAAGATACA CTTCCACAAG TAAGTGGTCA TAATGAAGGT   360
```

```
CAACAAACGA TTGAAGAAGA TACAACGCCG CCAACACCAC CAACACCAGA AGTACCAAGT      420

GAGCCGGAAA CACCAACACC ACCGACACCA GAAGTACCAA GTGAGCCGGA AACACCAACA      480

CCGCCAACAC CAGAGGTACC AAGTGAGCCG GAAACACCAA CACC                      524
```

(2) INFORMATION FOR SEQ ID NO: 10:

(i) SEQUENCE CHARACTERISTICS:
        (A) LENGTH: 174 amino acids
        (B) TYPE: amino acid
        (D) TOPOLOGY: linear (ii) MOLECULE TYPE: Protein (xi) SEQUENCE DESCRIPTION: SEQ ID NO: 10:

```
Gly Gln Asn Ser Gly Asn Gln Ser Phe Glu Glu Asp Thr Glu Glu Asp
 1               5                  10                  15

Lys Pro Lys Tyr Glu Gln Gly Gly Asn Ile Val Asp Ile Asp Phe Asp
            20                  25                  30

Ser Val Pro Gln Ile His Gly Gln Asn Lys Gly Asp Gln Ser Phe Glu
        35                  40                  45

Glu Asp Thr Glu Lys Asp Lys Pro Lys Tyr Glu His Gly Gly Asn Ile
50                  55                  60

Ile Asp Ile Asp Phe Asp Ser Val Pro His Ile His Gly Phe Asn Lys
65                  70                  75                  80

His Thr Glu Ile Ile Glu Glu Asp Thr Asn Lys Asp Lys Pro Asn Tyr
                85                  90                  95

Gln Phe Gly Gly His Asn Ser Val Asp Phe Glu Glu Asp Thr Leu Pro
            100                 105                 110

Gln Val Ser Gly His Asn Glu Gly Gln Gln Thr Ile Glu Glu Asp Thr
        115                 120                 125

Thr Pro Pro Thr Pro Pro Thr Pro Glu Val Pro Ser Glu Pro Glu Thr
    130                 135                 140

Pro Thr Pro Pro Thr Pro Glu Val Pro Ser Glu Pro Glu Thr Pro Thr
145                 150                 155                 160

Pro Pro Thr Pro Glu Val Pro Ser Glu Pro Glu Thr Pro Thr
                165                 170
```

(2) INFORMATION FOR SEQ ID NO:11:

(i) SEQUENCE CHARACTERISTICS:
        (A) LENGTH: 536 base pairs
        (B) TYPE: nucleic acid
        (C) STRANDEDNESS: single
        (D) TOPOLOGY: linear (ii) MOLECULE TYPE: GENOMIC DNA (xi) SEQUENCE DESCRIPTION: SEQ ID NO:11:

```
GGCCAAAATA GCGGTAACCA GTCATTCGAG GAAGACACAG AAGAAGACAA ACCTAAATAT      60

GAACAAGGTG GCAATATCGT AGATATCGAT TTTGATAGTG TACCTCAAAT TCATGGTCAA      120

AATAAAGGTA ATCAGTCATT CGAGGAAGAT ACAGAAAAAG ACAAACCTAA GTATGAACAT      180

GGCGGTAACA TCATTGATAT CGACTTCGAC AGTGTGCCAC ATATTCACGG ATTCAATAAG      240

CACACTGAAA TTATTGAAGA AGATACAAAT AAAGATAAAC CAAGTTATCA ATTCGGTGGA      300

CACAATAGTG TTGACTTTGA AGAAGATACA CTTCCAAAAG TAAGCGGTCA AAATGAAGGT      360

CAACAAACGA TTGAAGAAGA TACAACACCT CCAATCGTGC CACCAACGCC ACCGACACCA      420

GAAGTACCAA GTGAGCCGGA AACACCAACG CCACCAACAC CAGAAGTACC AAGTGAGCCG      480
```

GAAACACCAA CACCACCGAC ACCAGAAGTG CCGAGTGAGC CAGAAACTCC AACACC        536

(2) INFORMATION FOR SEQ ID NO:12:

(i) SEQUENCE CHARACTERISTICS:
        (A) LENGTH: 178 amino acids
        (B) TYPE: amino acid
        (C) STRANDEDNESS: single
        (D) TOPOLOGY: linear (ii) MOLECULE TYPE: Protein (xi) SEQUENCE DESCRIPTION: SEQ ID NO:12:

```
Gly Gln Asn Ser Gly Asn Gln Ser Phe Glu Glu Asp Thr Glu Glu Asp
  1               5                  10                  15

Lys Pro Lys Tyr Glu Gln Gly Gly Asn Ile Val Asp Ile Asp Phe Asp
                 20                  25                  30

Ser Val Pro Gln Ile His Gly Gln Asn Lys Gly Asp Gln Ser Phe Glu
             35                  40                  45

Glu Asp Thr Glu Lys Asp Lys Pro Lys Tyr Glu His Gly Gly Asn Ile
 50                  55                  60

Ile Asp Ile Asp Phe Asp Ser Val Pro His Ile His Gly Phe Asn Lys
 65                  70                  75                  80

His Thr Glu Ile Ile Glu Glu Asp Thr Asn Lys Asp Lys Pro Ser Tyr
                 85                  90                  95

Gln Phe Gly Gly His Asn Ser Val Asp Phe Glu Glu Asp Thr Leu Pro
                100                 105                 110

Lys Val Ser Gly Gln Asn Glu Gly Gln Gln Thr Ile Glu Glu Asp Thr
            115                 120                 125

Thr Pro Pro Ile Val Pro Pro Thr Pro Pro Thr Pro Glu Val Pro Ser
130                 135                 140

Glu Pro Glu Thr Pro Thr Pro Pro Thr Pro Glu Val Pro Ser Glu Pro
145                 150                 155                 160

Glu Thr Pro Thr Pro Pro Thr Pro Glu Val Pro Ser Glu Pro Glu Thr
                165                 170                 175

Pro Thr
```

(2) INFORMATION FOR SEQ ID NO:13:

(i) SEQUENCE CHARACTERISTICS:
        (A) LENGTH: 174 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:13:

```
Gly Gln Asn Ser Gly Asn Gln Ser Phe Glu Glu Asp Thr Glu Glu Asp
  1               5                  10                  15

Lys Pro Lys Tyr Glu Gln Gly Gly Asn Ile Val Asp Ile Asp Phe Asp
                 20                  25                  30

Ser Val Pro Gln Ile His Gly Gln Asn Lys Gly Asp Gln Ser Phe Glu
             35                  40                  45

Glu Asp Thr Glu Lys Asp Lys Pro Lys Tyr Glu Gln Gly Gly Asn Ile
 50                  55                  60

Ile Asp Ile Asp Phe Asp Ser Val Pro His Ile His Gly Phe Asn Lys
 65                  70                  75                  80

His Thr Glu Ile Ile Glu Glu Asp Thr Asn Lys Asp Lys Pro Asn Tyr
```

-continued

```
                85                  90                  95
Gln Phe Gly Gly His Asn Ser Val Asp Phe Glu Glu Asp Thr Leu Pro
            100                 105                 110

Gln Val Ser Gly His Asn Glu Gly Gln Gln Thr Ile Glu Glu Asp Thr
        115                 120                 125

Thr Pro Pro Ile Val Pro Pro Thr Pro Pro Thr Pro Glu Val Pro Ser
    130                 135                 140

Glu Pro Glu Thr Pro Thr Pro Pro Thr Pro Glu Val Pro Ser Glu Pro
145                 150                 155                 160

Glu Thr Pro Thr Pro Pro Thr Pro Glu Val Pro Thr Glu Pro
                165                 170
```

(2) INFORMATION FOR SEQ ID NO:14:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:14:

```
Pro Ile Val Pro
1
```

(2) INFORMATION FOR SEQ ID NO:15:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:15:

```
Pro Pro Ile Val Pro Pro Thr
1               5
```

FIBRONECTIN BINDING PROTEIN POLYPEPTIDES

This is a continuation of PCT application Ser. No. PCT/GB94/00215 filed Feb. 4, 1994 which claimed priority from GB9302289.5 filed on Feb. 5, 1993 and GB9321592.9 filed Oct. 20, 1993.

FIELD OF THE INVENTION

The present invention relates to novel polypeptides and monoclonal antibodies, their preparation and their use to combat infection at the site of wounds, surgical implants and other in-dwelling devices such as catheters. The present invention also relates to isolated nucleic acids encoding the polypeptide and to recombinant host cells transformed with DNA encoding the polypeptide.

BACKGROUND OF THE INVENTION

One of the major complications associated with the clinical use of implanted materials and in-dwelling devices is bacterial infection. In particular, staphylococci have frequently been implicated in medical device-related infections (Dankert et al 1986, CRC Rev Biocompatability 2, 219–301). Once established the infection is virtually impossible to treat resulting in implant failure.

It has been suggested that the adhesion of a microorganism to a surface is an initial step in the development of such infections (Quie and Belani, 1987, J. Infec. Dis. 156: 543–547) and there is now evidence to suggest that a specific adhesion mechanism is involved in the pathogenesis of foreign body infections (Vaudaux et al. 1990, J. Biomat. Appl. 5: 134–153). Soon after coming into contact with blood, inert materials, such as used for intravenous cannulae and prosthetic implants, are almost immediately coated with a layer of extracellular matrix proteins, (Cottanaro et al 1981, Transactions of the American Society for Artificial Internal Organs 27: 391–395). In particular this layer includes the plasma protein fibronectin and it is believed that staphylococci are able to bind to fibronectin through bacterial cell surface receptor proteins known as fibronectin binding protein (Fbp). However, some studies have suggested that blood proteins do not promote adherence of staphylococci to biomaterial (eg. Muller et al 1991, Infect.Immun. 59: 3323–3326) thereby discouraging research into the interaction of these bacteria with these proteins as an approach in the prevention of adhesion to biomaterials.

Fibronectin binding proteins have been isolated from *Staphylococcus aureus* and the nucleotide sequence subsequently established [Signas, C. et al. (1989) Proc. Nat. Acad. Sci 86, 699–703; Jonsson, K. et al. (1991) Eur. J. Biochem. 202, 1041–1048] (FbpA and FbpB respectively). The primary fibronectin binding domain of this protein has been identified as a homologous unit (usually of 38 amino acids) that is repeated three times (D1–D3 region) and partially repeated a fourth time (D4 region).

Previous attempts to combat staphylococcal adhesion to implants have involved modification of the surface of the prosthetic material to discourage adhesion of proteins; e.g. coating with a "non-stick" material such as PTFE, or bonding antibiotics to the surface (Kamal et al., 1991, J. Amer. Med. Assoc. 265, 2364–2368).

There have also been proposals to use non-steroidal anti-inflammatory drugs to prevent adhesion of staphylococci to medical polymers (Farber and Wolff 1992, J. Infect. Dis. 166: 861–865).

EP0163623, EP0294349, EP0397633 and WO92/02555 disclose certain fibronectin binding polypeptides from *S. aureus*.

Figure 1:
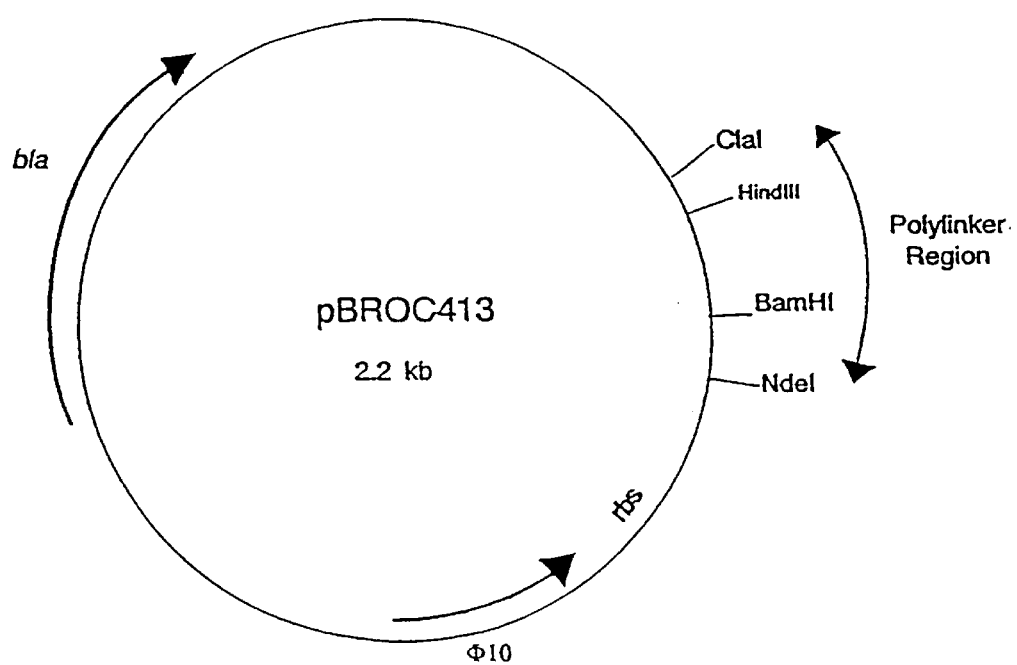
FIG. 1. is a diagrammatic presentation of plasmid pBROC413. Bla indicates the ampicillin resistance gene, φ10 the T7 RNA polymerase promoter and rbs the ribosome binding site. Arrows for φ10 and bla give the direction of transcription. The polylinker site has been indicated. The plasmid is not drawn to scale and the size is approximate.

One approach adopted in the present invention is to use a monoclonal antibody that binds to matrix binding proteins, such as fibronectin binding protein, to block the adhesion of bacteria to matrix proteins.

Accordingly, in one broad aspect the present invention is directed to the use of a monoclonal antibody (Mab), or a fragment thereof, that binds to one or more epitopes of a matrix binding protein in the prevention of adhesion of bacteria, in particular gram positive bacteria, to extracellular matrix proteins on in-dwelling devices or to extracellular matrix proteins in wounds. The invention particularly relates to the manufacture of a medicament for such uses.

The effect of the Mab or fragment is to block the site on the matrix binding protein that is associated with binding to the matrix protein.

In-dwelling devices include surgical implants, prosthetic devices and catheters, i.e., devices that are introduced to the body of a patient and remain in position for an extended time. Such devices include, for example, artificial joints, heart valves, pacemakers, vascular grafts, vascular catheters, cerebrospinal fluid shunts, urinary catheters, continuous ambulatory peritoneal dialysis (CAPD) catheters, etc.

The invention is particularly concerned with the use of monoclonal antibodies that will prevent the adhesion of staphylococci such as *S. aureus* and coagulase-negative staphylococci, such as *S. epidermidis* to such indwelling devices. Accordingly the monoclonal antibody is preferably directed against epitopes of matrix binding proteins derived from such bacteria.

Preferably the matrix binding protein to be recognised by the monoclonal antibody is fibronectin binding protein. In fibronectin binding protein it is known that a region identified as the D1–D4 domain is especially relevant in binding to fibronectin (Signas. C et al. 1989 op. cit).

Accordingly, in a preferred embodiment the monoclonal antibody is directed against an epitope present on the D1–D4 domain of fibronectin binding protein or a component unit thereof.

Novel monoclonal antibodies described above and their fragments form a further aspect of the invention.

The antibody may be either intact antibody of $M_r$ approx 150,000 or a derivative of it, for example a Fab fragment or a Fv fragment as described in Skerra, A and Pluckthun, A (1988) Science 240 1038–1040. If two antigen binding domains are present each domain may be directed against a different epitope—termed 'bispecific' antibodies.

The antibody or derivative thereof may be prepared by conventional means for example by established monoclonal antibody technology (Kohler, G. and Milstein, C. (1975), Nature, 256,495–497) or using recombinant means e.g. combinatorial libraries, for example as described in Huse, W. D. et al., (1989) Science 246,1275–1281.

Preferably the antibody or derivative is prepared by expression of a DNA polymer encoding said antibody in an appropriate expression system. The choice of vector for the expression system will be determined in part by the host, which may be a prokaryotic cell, such as *E. coli* (preferably strain B) or Streptomyces sp. or a eukaryotic cell, such as a mouse C127, mouse myeloma, human HeLa, Chinese hamster ovary, filamentous or unicellular fungi or insect cell. The host may also be a transgenic animal or a transgenic plant [for example as described in Hiatt,A et al.,(1989) Nature 34, 76–78]. Suitable vectors include plasmids, bacteriophages, cosmids and recombinant viruses, derived from, for example, baculoviruses and vaccinia.

The Fab fragment may also be prepared from its parent monoclonal antibody by enzyme treatment, for example using papain to cleave the Fab portion from the Fc portion.

The monoclonal antibody may be generated initially using as immunogen fibronectin binding protein, or the D1–D4 region of fibronectin binding protein (SEQ ID NO. 6, 7, and 8).

Fibronectin binding protein of *Staphylococcus aureus* is known to exist in at least two variants FbpA and FbpB [Jonsson et al.(1991), op. cit.].

The binding domain of either of the above fibronectin binding proteins may be used as immunogen to generate a Mab of this invention.

We believe we have now identified as a novel compound a new fibronectin binding protein from *S. aureus* J2385 (see Example 2 in particular) (SEQ ID NO. 10).

In particular we have isolated as a novel compound a polypeptide comprising essentially the D1–D4 region of the Fbp of *S. aureus* J2385 (SEQ ID NO: 11).

*Staphylococcus aureus* J2385 has been deposited at the National Collection of Industrial and Marine Bacteria Ltd. (NCIMB), Aberdeen, Scotland under number NCIMB 40532 on Dec. 18 th 1992.

The D1–D4 region has the amino acid sequence set out in Table 2 below.

This new Fbp and D1–D4 polypeptide (SEQ ID NO. 6, 7, and 8) and antigenically or immunologically equivalent derivatives thereof form a further aspect of this invention.

The term 'antigenically equivalent derivative' as used herein encompasses a peptide or its equivalent which will be specifically recognised by certain antibodies which, when raised to peptides according to the present invention, block adhesion of staphylococci to in-dwelling medical devices.

The term 'immunologically equivalent derivative' as used herein encompasses a peptide or its equivalent which when used in a suitable formulation to raise antibodies in a vertebrate, the antibodies act to block adhesion of staphylococci to in-dwelling medical devices.

In particular derivatives which are slightly longer or slightly shorter than the peptide of the present invention may be used. In addition, peptides in which one or more of the amino acid residues are modified before or after the peptide is synthesised may be used. Such peptides may, for example, be prepared by substitution, addition, or rearrangement of amino acids or by chemical modification thereof. All such substitutions and modifications are generally well known to those skilled in the art of peptide chemistry.

The D1–D4 polypeptide (SEQ ID NO. 6, 7 and 8) may be obtained by expression in *Escherichia coli* of the plasmid pBROC520. The preparation of this plasmid and the expression and purification of D1–D4 polypeptides (SEQ ID NO. 6, 7 and 8) and are described below in the Examples.

The DNA encoding this polypeptide is another aspect of this invention. The nucleotide sequence is shown in Table 1 below.

Other D1–D4 polypeptides (SEQ ID NO. 6, 7 and 8) e.g. of FbpA and FbpB, can be similarly expressed by analogous preparation of appropriate plasmids from chromosomal DNA.

The DNA encoding the D1–D4 polypeptide (SEQ ID NO. 6, 7 and 8) of FbpA is shown in Table 1 below.

The D1–D4 polypeptide, or an antigenically or immunologically equivalent polypeptide or a fusion protein thereof is used as an antigen to immunize a mouse or other animal such as a rat or chicken. The fusion protein may provide stability to the polypeptide. The antigen may be associated, for example by conjugation, with an immunogenic carrier protein for example bovine serum albumin (BSA) or keyhole limpet haemocyanin (KLH). Alternatively a multiple antigenic peptide comprising multiple copies of the D1–D4 polypeptide (SEQ ID NO. 6, 7 and 8), or an antigenically or immunologically equivalent polypeptide thereof may be sufficiently antigenic to improve immunogenicity so as to obviate the use of a carrier.

Using the procedure of Kohler and Milstein (1975 Nature 256,495–497), antibody-containing cells from the immunised mammal are fused with myeloma cells to create hybridoma cells secreting monoclonal antibodies.

The hybridomas are screened to select a cell line with high binding affinity and favorable cross reaction with other staphylococcal species using one or more of the original Fbp, D1–D4 polypeptide (SEQ ID NO. 6, 7 and 8) and/or the fusion protein. The selected cell line is cultured to obtain the desired Mab.

Hybridoma cell lines secreting the monoclonal antibody are another aspect of this invention.

Alternatively phage display technology could be utilised to select antibody genes with binding activities towards Fbp or D1–D4 either from repertoires of PCR amplified v-genes of lymphocytes from humans screened for possessing anti-Fbp or from naive libraries (McCafferty, J. et al., (1990), Nature 348, 552–554; Marks, J. et al., (1992) Biotechnology 10, 779–783). The affinity of these antibodies can also be improved by chain shuffling (Clackson, T. et al., (1991) Nature 352, 624–628).

Preferably the antibody or derivative thereof is modified to make it less immunogenic in the patient. For example, if the patient is human the antibody may most preferably be 'humanised'; where the complimentarily determining region (s) of the hybridoma-derived antibody has been transplanted into a human monoclonal antibody, for example as described in Jones, P. et al (1986), Nature 321, 522–525 or Tempest et al.,(1991) Biotechnology 9, 266–273.

The modification need not be restricted to one of 'humanisation'; other primate sequences (for example Newman, R. et al. 1992, Biotechnology,10, 1455–1460) may also be used.

The antibody should be screened again for high affinity to Fbp, D1–D4 polypeptide (SEQ ID NO. 6, 7 and 8) and/or fusion protein.

As mentioned above, a fragment of the final antibody may be prepared.

The humanised monoclonal antibody, or its fragment having binding activity, form a further aspect of this invention.

In another broad aspect the invention provides an isolated D1–D4 polypeptide (SEQ ID NO:6, 7 and 8) from a *Staphylococcus aureus* Fbp and its use in the prevention of adhesion of bacteria, in particular gram positive bacteria, to extracellular matrix proteins on in-dwelling devices or to extracellular matrix proteins in wounds. The invention further relates to the manufacture of a medicament for such uses.

In particular the gram positive bacteria include staphylococci such as *S. aureus* and coagulase-negative staphylococci, such as *S. epidermidis*.

By isolated D1–D4 polypeptide (SEQ ID NO: 6, 7 and 8) is meant a polypeptide consisting of the entire D1, D2, D3 and D4 regions optionally terminating in PIVP and optionally from one to five wall regions (WR) of *Staphylococcus aureus* Fbp, in sequence.

Depending upon the host expression system, the polypeptide may include an N-terminal methionine residue.

The above regions correspond to the following regions of FbpA as described in Signas et al. (1989), op. cit.:

| D1 | G709-H746 | WR1 | P843-T856 |
|----|-----------|-----|-----------|
| D2 | G747-H784 | WR2 | P857-T870 |
| D3 | G785-S823 | WR3 | P871-T884 |
| D4 | G824-P838 | WR4 | P885-K898 |
|    |           | WR5 | P899-K912 |

In a preferred aspect, the polypeptide contains up to three wall regions. Preferred embodiments consist of residues corresponding to residues G709 to T886 and G709 to P838 (optionally where P838→T) of *Staphylococcus aureus* FbpA (SEQ ID NO. 13). The Fbp is preferably from *Staphylococcus aureus* J2385 with sequence given in Table 2 (SEQ ID NO: 14 and 15).

This invention also provides isolated nucleic acid molecules encoding the polypeptide, including mRNAs, DNAs and cDNAs.

This invention also provides recombinant vectors, such as cloning and expression plasmids useful as reagents in the recombinant production of the polypeptides as well as recombinant prokaryotic and/or eukaryotic host cells comprising the novel nucleic acid sequence.

This invention also provides transgenic non-human animals comprising a nucleic acid molecule encoding the polypeptide.

A "replicon" is any genetic element (e.g., plasmid, chromosome, virus) that functions as an autonomous unit of DNA replication in vivo; i.e., capable of replication under its own control.

A "vector" is a replicon, such as a plasmid, phage, or cosmid, to which another DNA segment may be attached so as to bring about the replication of the attached segment.

A "double-stranded DNA molecule" refers to the polymeric form of deoxyribonucleotides (bases adenine, guanine, thymine, or cytosine) in a double-stranded helix, both relaxed and supercoiled. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having the sequence homologous to the mRNA).

A DNA "coding sequence of" or a "nucleotide sequence encoding" a particular protein, is a DNA sequence which is transcribed and translated into a polypeptide when placed under the control of appropriate regulatory sequences.

A "promoter sequence" is a DNA regulatory region capable of binding RNA polymerase in a cell and initiating transcription of a downstream (3' direction) coding sequence. For purposes of defining the present invention, the promoter sequence is bound at the 3' terminus by a translation start codon (e.g., ATG) of a coding sequence and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

DNA "control sequences" refers collectively to promoter sequences, ribosome binding sites, polyadenylation signals, transcription termination sequences, upstream regulatory domains, enhancers, and the like, which collectively provide for the expression (i.e., the transcription and translation) of a coding sequence in a host cell.

A control sequence "directs the expression" of a coding sequence in a cell when RNA polymerase will bind the promoter sequence and transcribe the coding sequence into mRNA, which is then translated into the polypeptide encoded by the coding sequence.

A "host cell" is a cell which has been transformed or transfected, or is capable of transformation or transfection by an exogenous DNA sequence.

A cell has been "transformed" by exogenous DNA when such exogenous DNA has been introduced inside the cell membrane. Exogenous DNA may or may not be integrated (covalently linked) into chromosomal DNA making up the genome of the cell. In prokaryotes and yeasts, for example, the exogenous DNA may be maintained on an episomal element, such as a plasmid. With respect to eukaryotic cells, a stably transformed or transfected cell is one in which the exogenous DNA has become integrated into the chromosome so that it is inherited by daughter cells through chromosome replication. This stability is demonstrated by the ability of the eukaryotic cell to establish cell lines or clones comprised of a population of daughter cell containing the exogenous DNA.

A "clone" is a population of cells derived from a single cell or common ancestor by mitosis. A "cell line" is a clone of a primary cell that is capable of stable growth in vitro for many generations.

A "heterologous" region of a DNA construct is an identifiable segment of DNA within or attached to another DNA molecule that is not found in association with the other molecule in nature.

This invention provides an isolated nucleic acid molecule encoding the polypeptide. The isolated nucleic acids particularly the DNAs can be introduced into expression vectors by operatively linking the DNA to the necessary expression control regions (e.g. regulatory regions) required for gene expression. The vectors can be introduced into the appropriate host cells such as prokaryotic (e.g., bacterial), or eukaryotic (e.g. yeast, insect or mammalian) cells by methods well known in the art (Ausubel et al.,supra). The coding sequences for the desired proteins having been prepared or isolated, can be cloned into a suitable vector or replicon. Numerous cloning vectors are known to those of skill in the art, and the selection of an appropriate cloning vector is a matter of choice. Examples of recombinant DNA vectors for cloning and host cells which they can transform include the bacteriophage λ (*E. coli*), pBR322 (*E. coli*), pACYC177 (*E. coli*), pKT230 (gram-negative bacteria), pGV1106 (gram-negative bacteria), pLAFR1 (gram-negative bacteria), pME290 (non-*E. coli* gram-negative bacteria), pHV14 (*E.* coli and Bacillus subtilis), pBD9 (Bacillus), pIJ61 (Streptomyces), pUC6 (Streptomyces), YIp5 (Saccharomyces), a baculovirus insect cell system, , YCp19 (Saccharomyces). See, generally, "DNA Cloning": Vols. I & II, Glover et al. ed. IRL Press Oxford (1985) (1987) and; T. Maniatis et al. ("Molecular Cloning" Cold Spring Harbor Laboratory (1982).

The gene can be placed under the control of a promoter, ribosome binding site (for bacterial expression) and, optionally, an operator (collectively referred to herein as "control" elements), so that the DNA sequence encoding the desired protein is transcribed into RNA in the host cell transformed by a vector containing this expression construction. The coding sequence may or may not contain a signal peptide or leader sequence. The polypeptides of the present invention can be expressed using, for example, the E. coli tac promoter or the protein A gene (spa) promoter and signal sequence. Leader sequences can be removed by the bacterial host in post-translational processing. See, e., U.S. Pat. Nos. 4,431,739; 4,425,437; 4,338,397.

In addition to control sequences, it may be desirable to add regulatory sequences which allow for regulation of the expression of the protein sequences relative to the growth of the host cell. Regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

An expression vector is constructed so that the particular coding sequence is located in the vector with the appropriate regulatory sequences, the positioning and orientation of the coding sequence with respect to the control sequences being such that the coding sequence is transcribed under the "control" of the control sequences (i.e., RNA polymerase which binds to the DNA molecule at the control sequences transcribes the coding sequence). Modification of the coding sequences may be desirable to achieve this end. For example, in some cases it may be necessary to modify the sequence so that it may be attached to the control sequences with the appropriate orientation; i.e., to maintain the reading frame. The control sequences and other regulatory sequences may be ligated to the coding sequence prior to insertion into a vector, such as the cloning vectors described above. Alternatively, the coding sequence can be cloned directly into an expression vector which already contains the control sequences and an appropriate restriction site.

In some cases, it may be desirable to add sequences which cause the secretion of the polypeptide from the host organism, with subsequent cleavage of the secretory signal.

A number of prokaryotic expression vectors are known in the art. See, e.g., U.S. Pat. Nos. 4,578,355; 4,440,859; 4,436,815; 4,431,740; 4,431,739; 4,428,941; 4,425,437; 4,418,149; 4,411,994; 4,366,246; 4,342,832; see also U.K. Patent Applications GB 2,121,054; GB 2,008,123; GB 2,007,675; and European Patent Application 103,395. Yeast expression vectors are also known in the art. See, e.g, U.S. Pat. Nos. 4,446,235; 4,443,539; 4,430,428; see also European Patent Applications 103,409; 100,561; 96,491. pSV2neo (as described in J. Mol. Appl. Genet. 1: 327–341) which uses the SV40 late promoter to drive expression in mammalian cells or pCDNA1neo, a vector derived from pCDNA1(Mol. Cell Biol. 7: 4125–29) which uses the CMV promoter to drive expression. Both these latter two vectors can be employed for transient or stable(using G418 resistance) expression in mammalian cells. Insect cell expression systems, e.g., Drosophila, are also useful, see for example, PCT applications WO 90/06358 and WO 92/06212 as well as EP application EP0290261.

Depending on the expression system and host selected, the polypeptide of the present invention may be produced by growing host cells transformed by an expression vector described above under conditions whereby the polypeptide of interest is expressed. The polypeptide is then isolated from the host cells and purified. If the expression system secretes the polypeptide into growth media, the polypeptide can be purified directly from the media. If the polypeptide is not secreted, it is isolated from cell lysates or recovered from the cell membrane fraction. The selection of the appropriate growth conditions and recovery methods are within the skill of the art.

Another aspect of the invention is a pharmaceutical composition comprising the above D1–D4 polypeptide (SEQ ID NO. 6, 7 and 8) and or Mab or active fragment and a pharmaceutically acceptable carrier.

In therapy or as a prophylactic, the D1–D4 polypeptide (SEQ ID NO. 6, 7 and 8) or Mab or fragment may be administered to a patient as an injectable composition, for example as a sterile aqueous dispersion, preferably isotonic.

Alternatively the composition may be formulated for topical application for example in the form of ointments, creams, lotions, eye ointments, eye drops, ear drops, mouthwash, impregnated dressings and sutures and aerosols, and may contain appropriate conventional additives, including, for example, preservatives, solvents to assist drug penetration, and emollients in ointments and creams. Such topical formulations may also contain compatible conventional carriers, for example cream or ointment bases, and ethanol or oleyl alcohol for lotions. Such carriers may constitute from about 1% to about 98% by weight of the formulation; more usually they will constitute up to about 80% by weight of the formulation.

The composition of the invention may be administered by injection to achieve a systemic effect against relevant bacteria shortly before insertion of an in-dwelling device. Treatment may be continued after surgery during the in-body time of the device. In addition, the composition could also be used to broaden perioperative cover for any surgical technique to prevent staphylococcal wound infections.

Many orthopaedic surgeons consider that patients with prosthetic joints should be considered for antibiotic prophylaxis before dental treatment that could produce a bacteraemia. Late deep infection is a serious complication sometimes leading to loss of the prosthetic joint and is accompanied by significant morbidity and mortality. It may therefore be possible to extend the use of the D1–D4 polypeptide (SEQ ID NO. 6, 7 and 8) or a therapeutic monoclonal antibody as a replacement for prophylactic antibiotics in this situation.

For administration to human patients, it is expected that the daily dosage level of the active agent will be from 0.01 to 10 mg/kg, typically around 1 mg/kg. The physician in any event will determine the actual dosage which will be most suitable for an individual patient and will vary with the age, weight and response of the particular patient. The above dosages are exemplary of the average case. There can, of course, be individual instances where higher or lower dosage ranges are merited, and such are within the scope of this invention.

With the indicated dose range, no adverse toxicological effects will be observed with the compounds of the invention which would preclude their administration to suitable patients.

In addition to the therapy described above, the compositions of this invention may be used generally as a wound treatment agent to prevent adhesion of bacteria to matrix proteins, especially fibronectin, exposed in wound tissue and for prophylactic use in dental treatment as an alternative to, or in conjunction with, antibiotic prophylaxis. Alternatively, the composition of the invention may be used to bathe an indwelling device immediately before insertion. The active agent will preferably be present at a concentration of 1 μg/ml to 10 mg/ml for bathing of wounds or indwelling devices.

The Mabs or fragments described above may also be used as diagnostic reagent to detect the presence of bacteria containing Fbp, of Fbp itself, or the D1–D4 polypeptide of Fbp (SEQ ID NO. 6, 7 and 8).

Also while the monoclonal antibody aspects of this invention have been described primarily in terms of using the D1–D4 polypeptide of Fbp to generate the antibodies, clearly Fbp itself can also be used as antigen in the initial immunisation programme.

The following Examples illustrate the preparation of D1–D4 polypeptides for use as antigens and as anti-adhesive agents.

EXAMPLES

Key Reagents used in the Preparation, Isolation and Analysis of D1–D4 Polypeptides and Referred to in the Examples a) Construction of Vector pBROC413

The plasmid pT7-7[Tabor, S (1990), Current Protocols in Molecular Biology, F. A. Ausubel, Brent, R. E. Kingston, D. D. Moore, J. G. Seidman, J. A. Smith, and K. Struhl,eds.] pp.16.2.1–16.2.11. Greene Publishing and Wiley-Interscience,New York.] contains DNA corresponding to nucleotides 2065–4362 of pBR322 and like pBR322 can be mobilized by a conjugative plasmid in the presence of a third plasmid ColK. A mobility protein encoded by ColK acts on the nic site at nucleotide 2254 of pBR322 initiating mobilization from this point. pT7-7 was digested with LspI and BglII and the protruding 5' ends filled in with the Klenow fragment of DNA PolymeraseI. The plasmid DNA fragment was purified by agarose gel electrophoresis, the blunt ends ligated together and transformed into *E.coli* DH1 by electroporation using a Bio-Rad Gene Pulser and following the manufacturers recommended conditions. The resultant plasmid pBROC413 (FIG. 1) was identified by restriction enzyme analysis of plasmid DNA.

The deletion in pBROC413 from the LspI site immediately upstream of the φ10 promoter to the BglII site at nucleotide 434 of pT7-7 deletes the DNA corresponding to nucleotides 2065–2297 of pBR322. The nic site and adjacent sequences are therefore deleted making pBROC413 non mobilizable.

b) Preparation of Biotinylated Fibronectin Probe

Fibronectin (FN) was purified from a human plasma fraction (a gift from Dr. D. Pepper, Scottish Blood Transfusion Service) on Gelatin Sepharose, essentially as described by Miekka et al (1982) Thromb. Res. 27, 1–14. 11.2 mg FN (2.0 ml) in 0.05M Tris/0.1M NaCl pH7.5 was made 1.0 mg/ml by addition of 9.2 ml 0.05M $Na_2B_4O_7$ pH8.6 buffer. 80 μl of N-hydroxysuccinimidobiotin (Amersham UK) from a 5.0 mg/ml stock in dry dimethylformamide was added and the mixture incubated at room temperature for 1 h with constant agitation. The reaction was terminated by buffer exchange into Dulbecco's 'A' phosphate-buffered saline containing 0.1% (w/v) bovine serum albumin (BSA) using five Sephadex G25 columns (PD10, Pharmacia).

c) Synthesis of Fibronectin Sepharose CL4B 100 mg of human fibronectin, purified as described above, was coupled to 7 g of Cyanogen bromide-activated Sepharose CL4B (Pharmacia) at room temperature according to the manufacturers instructions, to yield 25 ml of gel matrix. Before use the FN-Sepharose was washed with all buffers used in the subsequent purification.

Numbering of Amino Acid Residues in the Examples

In the following examples the numbering of amino acid residues corresponds to the residues of FbpA according to Signas et al., (1989) op. cit. Residues 709–4838 of FbpA correspond to residues 1–130 of the sequence of *S. aureus* J2385 (SEQ ID NO: 13) given in Table 2 and residues 709–886 correspond to residues 1–174 (SEQ ID NO. 13).

Example 1

Isolation of DNA from *Staphylococcus aureus* J2385 Coding for the Fibronectin Binding Domains of Fibronectin Binding Protein

*S. aureus* J2385 is strain B described in Cookson et al. [1987] THE LANCET of August 15th. page 387. It is a clinical strain derived from a skin lesion. Chromosomal DNA was prepared by treating cells collected from an overnight shake flask culture with lysostaphin to lyse them and phenol/chloroform to remove cell protein. From this unpurified DNA preparation the fragment of DNA encoding the fibronectin binding domains of Fibronectin Binding Protein was obtained by a PCR amplification reaction. The oligonucleotide primers used in the PCR reaction were:

FIB 1 5'-GGGAATTCATATGGGCCAAAATAGCGGT AACCAGTC-3' (SEQ ID NO 1)
FIB 2 5'-GCGGATCCTTACGTTGGTGGCACGATT GGAGGTG-3' (SEQ ID NO 2)

PCR amplification was carried out using *S. aureus* J2385 chromosomal DNA (10 ng.) FIB 1 (1 micromolar), FIB 2 (1 micromolar), Tris-HCl pH8.3 (10 mM), KCl (50 mM), $MgCl_2$ (1.5 mM), gelatin (0.001%), Na dGTP (200 micromolar) Na dATP (200 micromolar), Na dTTP (200 micromolar), Na dCTP (200 micromolar) and Taq DNA Polymerase (2.5 units) in a final volume of 100 microliters made up with distilled water. The aqueous solution was overlaid with 80 microliters of liquid paraffin and subjected to 30 cycles of 94° C. (1 min.), 60° C. (1 min.) and 72° C. (2 min.) to enable the amplification to occur. When 10 microliters of the aqueous reaction were examined after amplification on 1.5% agarose gel electrophoresis in the presence of ethidium bromide (0.5 micrograms/ml.) it was observed by comparison to a sample of DNA fragments of known size that a single species of DNA fragment of approximately 500 basepairs was obtained.

Example 2

Obtaining the Sequence of the DNA Fragment Obtained by PCR Amplification of *S. aureus* J2385 Chromosomal DNA using Primers FIB 1 and FIB 2.

The size of the PCR fragment obtained (approx. 500 bp.) using conditions described in Example 1 was unanticipated as the primers FIB 1 and FIB 2 were designed to be homologous to sites in Fibronectin Binding Protein gene (as described by Signas C., et al. [1989] P.N.A.S. USA vol 86,699–703) of *S. aureus* which were reported to exist approximately 400 bp. apart. In order to authenticate the nature of the DNA fragment it was cloned into pUC19 and sequenced. The DNA from one PCR reaction was incubated with Eco RI and Bam HI restriction enzymes and cloned into similarly treated pUC19 [Yanisch -Perron, C. et al. (1985) Gene, 33, 103] and sequenced to create pBROC 519a. Because the PCR process occasionally introduces deletions and base substitutions into amplified DNA, similar clones of J2385 DNA were retained to consequence along with pBROC 519a for confirmation of results. pBROC 519a was sequenced in both strands using the SEQUENASE II kit obtained from United States Biochemical. The sequence obtained revealed the cloned fragment encoded 524 bp of S. aureus J2385 DNA. When the sequence was compared with that published by Signas et al. (loc. cit.) it was apparent that it was extensively homologous to region 2350–2885 of that S. aureus gene (using the Signas et al. numbering) but possessed significant differences (see Table 1). In particular, the derived amino acid sequence displayed amino acid differences to the published sequence at residues 752 (ASN→ASP), 803 (SER→ASN), 821 (LYS→GLN), 825 (GLN→HIS) and a four amino acid deletion (838→841), see Table 2 (SEQ ID NO 13). These differences were confirmed by sequencing independent clones of PCR amplified DNA. When the derived amino acid sequence from S. aureus J2385 DNA was compared to the corresponding regions in S. aureus Fibronectin binding protein type A (Signas et al. [1989]) and S. aureus type B protein (Jonsson et al. [1991] EUR. J. BIOCHEM. vol 202 pages 1041–1048) it was clear that the fibronectin binding domains of the S. aureus J2385 protein was very similar to the respective domains of both the type A and type B proteins but was identical to neither (Table 2 (SEQ ID NO. 13)). This suggested that the S. aureus J2385 protein should be denoted type C.

Example 3

Preparation of pBROC 520 in E. coli BL21 (DE3)

In order to express the protein fragment encoded by the cloned S.aureus J2385 DNA the T7 polymerase/promoter expression system as described by Tabor, S. was used (see Current Protocols in Molecular Biology [F. A. Ausubel, R. Brent, R. E. Kingston, D. D. Moore, J. G. Seidman, J. A. Smith and K. Struhl,eds.] pp.16.2.1–16.2.11. Greene Publishing and Wiley-Interscience, New York). The host was E. coli BL21(DE3) which inducibly expresses the T7 polymerase gene (see Studier F. W. and Moffat B. A. [1986] J.Mol.Biol. vol.189,113–130).

The 0.5 kb BamHI/NdeI fragment of S.aureus J2385 derived DNA was isolated from pBROC 519a (3 microgrammes) by restriction enzyme digestion and electrophoresis on low melting point agarose gel. This material (100 nanogrammes) was used in a ligation reaction with BamHI/NdeI digested pBROC 413 DNA (500 nanogrammes). The ligated DNA was electrotransformed into E. coli Delta M15 (see Sambrook, J., Fritsch, E. F. and Maniatis, T. editors [1989] Molecular Cloning, A Laboratory Manual (second edition) page 2.57 for details of the lacZ Delta M15 mutation) and transformants selected on LB agar containing ampicillin (50 microgrammes/ml.).

Plasmid DNA preparations were made from five ampicillin resistant colonies and were all shown by restriction enzyme site mapping to be pBROC 413 carrying the S.aureus derived DNA fragment. One of the plasmid preparations (designated pBROC 520) was used to transform E.coli BL21(DE3) to give the desired expression construct/host combination. pBROC 520 encodes the peptide given in SEQ ID NO 6, hereinafter referred to as D1–D4(709–886) (SEQ ID NO. 6).

Example 4

Expression, Isolation and Purification of D1–D4 (709–886) Polypeptide of J2385 Expressed from pBROC 520 in E. coli BL 21 (DE3)

a) Expression

Single colonies of E. coli BL 21 (DE3) harbouring either pBROC 413 (non-coding) plasmid or pBROC 520 (encoding D1–D4 (709–886)) were inoculated into 30 ml capped containers (universals) containing 10 ml of NZCYM medium (1% (w/v) Bactotryptone, 0.5% (w/v) Bacto yeast extract, 0.5% (w/v) NaCl, 0.1% (w/v) casamino acids and 0.2% (w/v) MgSO$_4$. 7 H$_2$O pH 7.0) and 75 μg/ml ampicillin. The cultures were incubated at 37° C., 230 rpm overnight. The overnight cultures were used to inoculate 250 ml NZCYM medium containing 150 μg/ml ampicillin. The cultures were incubated at 37° C., 230 rpm until A$_{600}$ reached 0.5 absorbance units. The cultures were then induced with 1 mM IPTG (Isopropylthio-β-D-galactoside) and incubated under the same conditions for a further 4 hours. 1 ml samples were removed pre-induction and 1,2,3 and 4 hours post-induction. Each sample was spun in an eppendorf centrifuge for 1 minute after which the supernatant was removed. The pellets were then resuspended in 100 μl of reducing buffer (50 mM Tris. HCl pH6.8, 100 mM dithiothreitol (DTT), 0.1% (w/v) bromophenol blue, 2% (w/v) SDS, 10% (v/v) glycerol) or non-reducing buffer (DTT is omitted). The samples were heated for 3 mins at 90° C. before being stored at –40° C.

b) Detection of Expressed Product

E. coli resuspended pellets containing either pBROC 413 (non-coding plasmid) or pBROC 520 (encoding D1–D4 (709–886)) were separated on sodium dodecyl sulphate containing 4–20% polyacrylamide gels (Novex, British Biotechnology Ltd.), essentially as described by the manufacturers. Separated proteins were transferred to Immobilon (Millipore (UK) Ltd.) using Sartoblot II blotting apparatus according to the manufacturer's instructions. Unreacted sites on the blot were blocked by incubation in 10 mM NaH$_2$PO$_4$/ 0.15M NaCl/0.02%($^w$/v) Ficoll/0.02%($^w$/v) polyvinylpyrrolidone/0.1%($^w$/v) bovine serum albumin (BSA) pH7.4 for 1 h at room temperature with constant agitation. The blot was probed with biotinylated fibronectin at 200 μg/ml in 0.02M NaH$_2$PO$_4$/0.3M NaCl/0.5%($^w$/v) Tween 80/1.0%($^w$/v) BSA pH7.4 for 4 h at room temperature with constant agitation. Bands were visualised using a Streptavidin Gold/silver stain system (Amersham UK) according to the manufacturer's instructions. Putative D1–D4 (709–886) polypeptide was identified as a new band in the pBROC 520 lane.

c) Isolation of Solubilised D1–D4 (709–886)

Frozen cell pellet of E. coli BL21 DE3 (pBROC 520)) (from a 300 ml culture) prepared essentially as described in a) above and using an induction period of 3 h was allowed to thaw at 4° C. for 2 h and was then resuspended in 50 mM Tris/50 mM NaCl/1 mM EDTA/0.1 mM phenyl methyl sulphonyl fluoride (PMSF) pH 8.0 (30 ml). The suspension was transferred to a 100 ml glass beaker and sonicated (Heat Systems—Ultrasonics W380; 70 Watts, 50×50% pulse, pulse time=5 sec). The sonicate was immediately centrifuged (6000 g/4° C./10 min) and the pellet discarded. The supernatant, containing the solubilised D1–D4 (709–886), was adjusted to pH 7.4 and retained at –40° C.

d) Purification of D1–D4 (709–886) (SEQ ID NO. 6) Product (i) D1–D4 (709–886) supernatant (SEQ ID NO. 6), prepared as described above, was applied to a FN-Sepharose column (1.6×13.2 cm) equilibrated in Dulbecco's 'A' phosphate-buffered saline (PBS)/0.4 M NaCl/ 0.1 mM PMSF. D1–D4 (709–886) (SEQ ID NO: 6) was eluted from the column with PBS/2M Guanidine.HCl and then concentrated by stirred cell ultrafiltration, using a $M_r$ 10,000 cut-off membrane (Amicon), to a 4.0 ml retentate. The D1–D4 (709–886) (SEQ ID NO. 6) retentate was formulated into product by buffer exchange into PBS using two Sephadex G25 columns (PD10, Pharamacia). 1.5 mg >90% pure, determined by RP-HPLC and SDS PAGE, D1–D4 (709–886) (SEQ ID NO. 6) product was obtained; material was confirmed as D1–D4 (709–886) by N-terminal sequencing and by Western blotting (probed with biotinylated fibronectin). The molecular weight of the isolated, purified polypeptide, determined by electrospray mass spectrophotometry was 19,970. The theoretical molecular weight is 19,969. Molecular weight analysis according to SDS PAGE indicated that the D1–D4 (709–886) (SEQ ID NO. 6) polypeptide had a mobility corresponding to a protein of approximately 35 000 (non-reduced) or approximately 40 000 (reduced); the protein markers used for this were the Low Molecular Weight Kit (Pharmacia).

(ii) An Alternative Purification Method was also Developed

D1–D4 (709–886) (SEQ ID NO.6 ) supernatant (from a 5 L culture), prepared essentially as described in Example 4c, was diluted 1:1 in 0.1M $NaH_2PO_4$ pH 7.6 (final pH adjusted to 7.6) and applied to a Q Sepharose (Pharmacia) column (i.d.,7.8 cm; h,5 cm) equilibrated in 0.1M $NaH_2PO_4$ pH 7.6. D1–D4 (709–886) (SEQ ID NO. 6) adsorbed to the column and was eluted using 0.1M $NaH_2PO_4$/0.5 M NaCl pH 7.6. It was then concentrated by stirred cell ultrafiltration, using a $M_r$10,000 cut-off membrane (Amicon), to a 30 ml retentate. At this stage D1–D4 (709–886) was approx. 50% pure. The D1–D4 (709–886) (SEQ ID NO. 6 ) retentate was buffer exchanged into 50 mM formic acid using a Sephadex G25 (Pharmacia) column (i.d.,2.6 cm; h,21 cm) to yield a 40 ml product. The D1–D4 (709–886) (SEQ ID NO. 6) product was further purified by four repeat runs on reverse-phase HPLC. Thus, 10 ml D1–D4 (709–886) (SEQ ID NO. 6) was applied to an Aquapore C4 column (Applied Biosystems) (i.d.,1 cm; h,10 cm) equilibrated in 0.1% trifluoroacetic acid (TFA). D1–D4 (709–886) (SEQ ID NO: 6) was eluted from the column using a 0 to 100% linear gradient of 0.085% TFA/70% acetonitrile, over 4–5 column volumes. The appropriate D1–D4 (709–886) (SEQ ID NO.6)-containing fractions from the four repeat runs were pooled and were concentrated by ultrafiltration (as above) to a 30 ml retentate. The D1–D4 (709–886) (SEQ ID NO. 6) retentate was formulated into final product by buffer exchange into 50 mM formic acid (as above) followed by lyophilisation.

50 mg ≧95% pure, determined by analytical reverse-phase HPLC and SDS PAGE, D1–D4 (709–886) product was obtained; material was confirmed as D1–D4 (709–886) (SEQ ID NO:6) by N-terminal sequencing and by Western blotting (probed with biotinylated fibronectin). The solubility of the D1–D4 (709–886) (SEQ ID NO. 6) lyophilised product was 35–40 mg/ml when reconstituted in $H_2O$ or 50 mM formic acid.

(iii) A Second Alternative Purification Method was Developed to Replace the C4 Reverse-Phase Step D1–D4 (709–886) (SEQ ID NO. 6) (48 ml) that had been eluted from a Q Sepharose column as described in (ii) was mixed with 4M $(NH_4)_2SO_4$ (16 ml) and applied to a Toyopearl Butyl column (TosoHaas) (i.d., 1.6 cm; h, 15 cm) equilibrated in 1.0M $(NH_4)_2SO_4$/0.1M $NaH_2PO_4$ pH7.0 (Buffer A). The column was then washed with approx. 3 bed volumes of Buffer A. The D1–D4 (709–886), which adsorbed to the matrix, was eluted from the column using a 30% to 100% linear gradient of 0.1M $NaH_2PO_4$ pH7.0 in Buffer A over 3 column volumes. The appropriate D1–D4 (709–886)-containing fractions were identified by SDS PAGE, were pooled and were then concentrated by ultrafiltration, using a $M_r$10,000 cut-off membrane (Amicon), to a 20 ml retentate. The D1–D4 (709–886) (SEQ ID NO. 6) retentate was formulated into final product by buffer exchange into 50 mM formic acid using a Sephadex G25 column (Pharmacia) (i.d., 2.6 cm; h, 21 cm) followed by lyophilisation.

50 mg ≧98% pure, determined by reverse-phase HPLC and SDS PAGE, D1–D4 (709–886) (SEQ ID NO. 6) product was obtained.

Example 5

Bioreactor Fermentation of D1–D4 (709–886) Polypeptide (SEQ ID NO.6)

Single colonies of *E.coli* BL21 (DE3):pBROC520 were recovered from LB agar medium containing 50 μg/ml ampicillin and used to inoculate 2×100 ml of seed medium (NCYZM) containing ampicillin at 75 μg/ml. The primary and secondary seed stage fermentations were carried out in 500 ml shake flasks batched with 100 ml aliquots of NCYZM medium. The primary and secondary seed fermentation conditions were as follows: 37° C., 230 rpm on an orbital shaker with a 50 mm throw. The primary seed incubation time was 9 hours. The primary seed culture was used to inoculate (0.1% v/v) 6×100 ml aliquots of secondary seed stage medium (NCYZM). The secondary seed was incubated for 14.5 hours.

Two 15 liter Biolafitte fermenters were each batched with 10 liters of NCYZM medium and 0.01% (v/v) Dow Corning DC1510 antifoam. The vessels plus media were sterilised using steam to 121° C. for 45 minutes. Ampicillin sterilised by microfiltration (0.2 μm) was added aseptically to the vessel media to a final concentration of 150 μg/ml. The fermenters were inoculated at a level of 2.5% (v/v) from pooled secondary seed culture. The final stage incubation conditions were 37° C., agitator 300 rpm, airflow 5 l/min (0.5 vvm). The final stage fermentations were sampled aseptically pre-inoculation, at 0 hours and thence approximately hourly. The samples were monitored for increases in optical density (550 nm). When the OD 550 was >=1.0, IPTG was added to give a final concentration of 1 mM. The fermentations were incubated for approximately a further 3 hours.

The cells were recovered by batch centrifugation using 7000 g for 35 minute, or continuous centrifugation at 15,000 g. The total cell yield was 73.5 grammes. Cells were washed once with a total of 1.0 liter of Oxoid phosphate buffered saline (Dulbecco 'A') pH 7.2. The centrifuged washed cells were then held frozen at −20° C. to await further processing.

| Composition of NCYZM medium: | |
|---|---|
| Difco Bacto Tryptone: | 10 g/l |
| Fisons AR NaCl: | 5 g/l |
| Difco Bacto Yeast Extract | 5 g/l |
| Difco Bacto Casamino Acids | 1 g/l |
| Fisons AR MgSO4.7H2o | 2 g/l |
| Deionised water | 950 ml |
| pH adjusted to 7.0 with 5M NaOH, then final volume to 1000 ml. | |

Example 6

Construction of pBROC 533, a Plasmid Expressing a Polypeptide Predominantly Consisting of the D1–D4 Domains (SEQ ID NO. 9) of S.aureus J2385 Fibronectin Binding Protein The following oligomeric polynucleotide (A) and its complement were synthesised on a Pharmacia LKB Gene Assembler Plus DNA synthesiser:

CGGAATTCGT CAACAAACGA TTGAAGAAGA TACAACGACG TAAGATCTGG ATCCGCATGC GAATTCCG [SEQ ID NO:13]

Samples of the two oligonucleotide preparations (0.14 microgrammes of each) were mixed, heated to 94 degrees C. for 5 minutes and then allowed to anneal at 37 degrees C for 10 minutes. The double stranded DNA was digested with EcoRI enzyme and subsequently cloned into the EcoRI site of pUC19 (2 microgrammes of EcoRI digested vector/ligation) to give pBROC 528 in E. coli Delta M15.

The BamHI digested kanamycin resistance marker of pUC4K (obtained from Pharmacia, code no. 27-4958-01) was then cloned into the unique BglII site of the resulting plasmid construct pBROC 528 to give pBROC 529.

pBROC 529 plasmid DNA (5 microgrammes) grown in E. coli Delta M15 was double digested with HincII/SphI and the approximately 1.4 kb DNA fragment encoding the kanamycin resistance gene and that moiety of Fibronectin Binding Protein encoded by the oligonucleotide originally synthesised was isolated using low melting point agarose/agarase. This DNA was used in a ligation reaction with partially digested HincII, completely digested SphI plasmid DNA (1 microgramme) of pBROC 519a (see Example 2). The ligation products were electrotransformed into E. coli Delta M15, selecting for kanamycin resistance. In this way, it proved possible to isolate pBROC 530, a plasmid which as ascertained by sequencing across the HincII sites of the staphylococcal DNA and by restriction mapping, carried a DNA fragment encoding the D1–D2–D3–D4 regions (SEQ ID NO. 13) (residues 1–129 in Table 2) of the Fibronectin Binding Protein of S. aureus J2385. The DNA fragment additionally coded for a threonine residue at the carboxy terminal of the polypeptide.

Next, the staphylococcal DNA of pBROC 530 was removed from the plasmid vector by NdeI/BamHI digestion of a plasmid DNA preparation and cloned into similarly digested pBROC413 (see Key reagents a) to give pBROC 531.

pBROC 531 was grown in a transformed strain of E. coli Delta M15 and then digested with SalI to remove the kanamycin resistance gene and subsequently religated to create pBROC 533. This step was carried out to prevent unnecessary overexpression of the kanamycin resistance gene from the T7 promoter in pBROC 531 as it was considered that this would be detrimental to maximal expression of the staphylococcal DNA.

pBROC 533 was transformed into E.coli BL21(DE3) to furnish E.coli BL21(DE3), pBROC533.

A variant of plasmid pBROC 531 may alternatively be constructed using the following oligomeric polynucleotide (B) and its complement:

CGGAATTCGT CAACAAACGA TTGAAGAAGA TACAACGCCG TAAGATCTGG ATCCGCATGC GAATTCCG [SEQ ID NO: 3]

This gives the same polypeptide as above with the terminal threonine replaced by proline.

Example 7

Expression, Isolation and Purification of D1–D4 (709–838(P838T)) Polypeptide Expressed from pBROC 533 in E.coli BL21(DE3)

a) Expression

This was carried out using the methods described in Example 4a), except that plasmid pBROC 533 from Example 6 was substituted for pBROC520.

b) Detection of Expressed Product

These were carried out using the methods described in Example 4b). D1–D4 (709–838(P838T)) (SEQ ID NO. 7) was identified as a new band in the pBROC 533 lane.

c) Isolation

This was carried out essentially as described in Example 4c), except that cell pellets of E.coli BL21 (DE3) (PBROC 533) were used, the starting volume of culture was 1.2 liters and the cell pellet was resuspended in 32 ml buffer. The final supernatant volume was 40 ml.

d) Purification

D1–D4 (709–838(P838T)) (SEQ ID NO. 7) supernatant, prepared as described above, was diluted 1:1 with 0.1M $NaH_2PO_4$ pH7.6, the pH adjusted to 7.6 using HCl and applied to a Q Sepharose (Pharmacia) column (i.d., 4.1 cm; h, 4.7 cm) equilibrated in 0.1M $NaH_2PO_4$ pH7.6. The polypeptide adsorbed to the column and was eluted using 0.1M $NaH_2PO_4$/0.5M NaCl pH7.6. Polypeptide solution (50 ml) that had eluted from the Q Sepharose was mixed with 4M $(NH_4)_2SO_4$ (16 ml) and applied to a Toyopearl Butyl column (TosoHaas) (i.d., 1.6 cm; h, 15 cm) equilibrated in 1.0M $(NH_4)_2SO_4$/0.1M $NaH_2PO_4$ pH7.0 (Buffer A). The column was then washed with approx. 3 bed volumes of Buffer A. The polypeptide, which adsorbed to the matrix, was eluted from the column using a 30% to 100% linear gradient of 0.1M $NaH_2PO_4$ pH7.0 in Buffer A over 3 column volumes. The appropriate polypeptide-containing fractions were identified by SDS PAGE, were pooled and were then concentrated by ultrafiltration, using a $M_r$10,000 cut-off membrane (Amicon), to a 20 ml retentate. The retentate was formulated into final product by buffer exchange into 50 mM formic acid using a Sephadex G25 column (Pharmacia) (i.d., 2.6 cm; h, 21 cm) followed by lyophilisation.

An aliquot of the lyophilisate was solubilised; the material showed a single major band of approximately $M_r$=22000 on SDS PAGE under non-reducing conditions.

Biological Evaluation

A. Effect of D1–D4 (709–886) (SEQ ID NO. 6) on Adhesion of Staphylococci to Fibronectin-coated Polymethylmethacrylate (PMMA) Coverslips in vitro.

(i) Bacterial strains

*Staphylococcus aureus* 8325-4 (standard laboratory strain)

*Staphylococcus aureus* J-2385

*Staphylococcus epidermidis* (SE 902 and SE 903, two clinical isolates from foreign body infection)

(ii) Adhesion Assay

The in vitro adhesion assay described by Vaudaux et al., Infection and Immunity 45: 768–774, 1984, was used to measure staphylococcal adhesion to fibronectin-coated surfaces and to test the anti-adhesive properties of the D1–D4 (709–886) polypeptide.

(iii) Preparation of Bacteria

Staphylococcal strains were grown overnight at 37° C. in Mueller-Hinton Broth (MHB, Difco Laboratories). A total of $2 \times 10^7$ cfu from the overnight culture was incubated with 100 μCi [methyl-$^3$H]-thymidine (Amersham) in 1 ml of MHB and grown for 3 hours at 37° C. up to $1 \times 10^8$–$2 \times 10^8$ cfu/ml. After removal of the unbound radioactivity by two washes (3,000×g, 10 minutes) the labelled strain was suspended in 1 ml of 0.15M NaCl.

(iv) Adsorption of Fibronectin to PMMA Coverslips

All PMMA coverslips (0.75 cm×0.75 cm) were immersed in 95% ethanol for 10 minutes at 37° C., drained and heated at 120° C. for 30 minutes. The coverslips were then preincubated with gelatin (1 mg/ml, Difco Laboratories) for 60 minutes at room temperature and rinsed with PBS (without $Ca^{2+}$–$Mg^{2+}$, Gibco Laboratories). Coverslips were immersed in solutions containing purified human fibronectin at two concentrations, 0.5 µg/ml for *S. aureus* strains and 4 µg/ml for *S. epidermidis* strains, for 60 minutes at 37° C. Coverslips were transferred to fresh tubes containing PBS and washed.

(v) Adhesion Assay

D1–D4 (709–886) polypeptide was diluted to the required concentration (ranging from 100 µg/ml to 10 pg/ml) in PBS supplemented with cations (Gibco Laboratories) and albumin (20%, Sigma) ($PBS^{++}$/HSA). Washed radiolabelled culture (40 µl) was added to 960 µl of the diluted D1–D4 (709–886) (SEQ ID NO. 6) polypeptide in plastic tubes. Fibronectin-coated coverslips were added to the bacterial suspensions and incubated at 37° C. for 60 minutes with shaking (100 cycles/minute)

Fluids were then drained away, coverslips transferred to fresh tubes, washed twice with saline (1 ml) at room temperature for 1×5 and 1×30 minutes. Fluids were drained away and coverslips transferred to scintillation vials supplemented with 5 ml scintillation fluid and counted.

(vi) Evaluation of cpm and cfu for each Strain

Portions of the 3 hour radiolabelled culture (10 µl) were counted in scintillation vials. 100 µl Aliquots were diluted 1 in 10,000 and 20 µl plated onto Mueller-Hinton agar and viable counted. In addition, the cpm content of the 100 µl of the diluted strain used in the adhesion assay was also checked to enable the numbers of cfu's adhering to fibronectin-coated PMMA coverslips to be calculated.

(vii) Results

| Conc. of D1-D4 (709-886) | Strain tested and % Adherence Inhibition | | |
|---|---|---|---|
| | *S. aureus* 8325.4* | *S. aureus* J2385* | *S. epidermidis* SE902** |
| 100 µg/ml | 97.5 | 78.4 | 95.7 |
| 10 µg/ml | 96.1 | 78.9 | 93.4 |
| 1 µg/ml | 95.8 | n/d | 91.9 |
| 100 ng/ml | 84.8 | n/d | 42.5 |
| 10 ng/ml | 94.4 | n/d | 0 |
| 1 ng/ml | 28.7 | n/d | 0 |

*Coverslips coated with 0.5 µg/ml of fibronectin
**Coverslips coated with 4.0 µg/ml of fibronectin

*S. aureus* 8325-4 is a standard strain which has been widely studied for its ability to adhere to a variety of materials coated with human fibronectin. The adhesion of this strain to fibronectin-coated surfaces is promoted when the surface is coated with increasing concentrations of fibronectin. Therefore, *S. aureus* 8325-4 was selected as being a suitable strain to test the effects of agents that might block the interaction between staphylococci and fibronectin-coated surfaces.

D1–D4 (709–886) (SEQ ID NO. 6) is a potent inhibitor of *S. aureus* 8325-4 adhesion to fibronectin-coated coverslips. Up to 95% adhesion inhibition could still be detected when the concentration of D1–D4 (709–886) (SEQ ID NO. 6) was reduced to 10 ng/ml. Purified human IgG (Pierce) was used as a control, since this has previously been shown to inhibit *S. aureus* adhesion to fibronectin-coated surfaces using this assay (Vaudaux et al. J. Invest. Surg, 2: 397–408 1989), and gave 70% inhibition at 1 mg/ml.

In addition, the adhesion of *S. aureus* J-2385 to fibronectin-coated coverslips is also promoted when increasing concentrations of fibronectin are used to coat the PMMA coverslips. However, the gelatin pretreatment of coverslips, described in the standard protocol, was omitted since it resulted in some non-specific binding which interfered with the adhesion assay. Demonstrating the adhesion of this strain to immobilised fibronectin is significant since the recombinant D1–D4 (709–886) polypeptide used in this study was derived from *S. aureus* J-2385. D1–D4 (709–886) polypeptide is capable of inhibiting adhesion of *S. aureus* J-2385 to fibronectin-coated surfaces.

The adhesion of *S. epidermidis* was also promoted when the concentration of fibronectin used to coat the coverslip was increased. It was noted that higher concentrations of fibronectin (4 µg/ml) were required to allow significant numbers of organisms to adhere when compared with *S. aureus* 8325-4 (0.5 µg/ml). The D1–D4 (709–886) polypeptide also inhibited adhesion of *S. epidermidis* to fibronectin (95% adhesion at 1 µg/ml) suggesting that D1–D4 (709–886) could have anti-adhesive activity as a therapeutic agent against coagulase-negative staphylococci.

B. Inhibition of *S. aureus* Adhesion to Dermal Substrates (i) Introduction

The dermal tissues used in this study was obtained as a kit (Skin$^2$) from Advanced Tissue Sciences (La Jolla, Calif., USA). Full details on growing the artificial dermis are supplied with the kit. The artificial dermis was formed by seeding human neonatal fibroblasts onto an inert medical grade nylon mesh. The fibroblasts adhere to the mesh and proliferate within the mesh interstices. During this process they secrete naturally occurring growth factors and deposit extracellular matrix proteins such as fibronectin and collagen thus developing into a human dermis. This model has been successfully used to represent the dermal tissues exposed in wounding.

(ii) In Vitro Dermal Adhesion Assay with *S. aureus* 8325-4

The procedure was essentially identical to that described above in A. except that samples of artificial dermis replaced the FN-coated coverslips. *S. aureus* 8325-4 was grown overnight in Mueller-Hinton Broth (MHB, Difco). A total of $2 \times 10^7$ cfu from the overnight culture was incubated with 100 µCi [methyl-$^3$H]-thymidine in 1 ml MHB and grown for 3 hours at 37° C. up to $1 \times 10^8$ to $2 \times 10^8$ cfu/ml. After removal of the free radioactivity by two centrifugations (3,000×g, 10 minutes) the labelled strain was suspended in 0.5% HSA (Sigma) to prevent non-specific binding to cellular/matrix proteins. The dermal substrates were washed with serum-free media and PBS prior to the addition of the radiolabelled bacteria.

(iii) Effect of D1–D4 (709–886) (SEQ ID NO. 6) on Adhesion to Dermal Substrates

D1–D4 (709–886) polypeptide was diluted to the required concentration in PBS supplemented with cations (Gibco Laboratories) and human serum albumin (20%, Sigma) ($PBS^{++}$-HSA). Washed bacteria (40 µl) were added to diluted samples of D1–D4 (709–886) (SEQ ID NO. 6) (960 µl). The dermal tissues were then added to the bacterial suspensions containing D1–D4 (709–886) (SEQ ID NO. 6) and incubated at 37° C. with shaking (100 cycles/minute). Fluids were drained away, dermal tissues were transferred to fresh tubes, washed with saline (1 ml) at room temperature for 5 and 30 minutes respectively. Fluids were drained away and dermal tissues transferred to scintillation vials supplemented with 5 ml scintillation fluid and counted.

(iv) Results

D1–D4 (709–886) (SEQ ID NO. 6) has a concentration-dependent inhibitory effect on the adhesion of *S. aureus* 8325-4 to dermal tissues. Significant adhesion inhibition was achieved (>50%) at concentrations of D1–D4 (709–886) (SEQ ID NO. 6) down to 1 μg/ml. These results show a good correlation to those obtained with the fibronectin-coated PMMA coverslip adhesion assay. In addition, the results confirm the importance of the interaction between *S. aureus* and fibronectin present in dermal tissues. As a consequence of this observation D1–D4 (709–886) (SEQ ID NO. 6) polypeptide may also be useful prophylactically as a topical application in the prevention of wound infections during surgery.

C. Inhibition of Adhesion of Staphylococci to Nylon Cannulae during Subcutaneous Implantation in the Rat.

(i) In Vivo Model of Experimental Foreign Body Infection

Male CD rats (Charles River (U.K.) Limited) weighing 230–250 g were used in this study. Three or four flexible vinyl cannulae (1.5 mm×2 cm) were subcutaneously implanted in each rat under sterile conditions. Animals were anaesthetised with Hypnorm (0.05 ml) i.m. followed by 0.05 ml i.m. valium. A 1 cm incision was made in centre of back to side of spine and a subcutaneous area was opened by blunt dissection. The cannulae were implanted and the incision was closed with clips. The wound was sprayed with Xylocaine prior to recovery from anaesthesia. The clips were removed after 6 days. The implant site was infected by dispensing bacterial culture (see below) into the wound during insertion of the cannulae.

(ii) Preparation of Bacteria for use in Infection Model

Bacteria were grown overnight in MHB (Difco). Overnight culture (20 μl) was used to inoculate fresh MHB (1 ml) and the culture was grown at 37° C. for 3 h or 16 h (exponential phase culture). The cells were washed twice(9,000×g, 10 minutes) and resuspended in 0.85% PBS (1 ml) to give 8.3 $\log_{10}$ cfu/ml. The bacterial suspensions were diluted 1 in 10 to give approximately 7 $\log_{10}$ cfu/ml and 0.1 ml of this suspension was used to infect the rats. Therefore, each wound was infected with approximately 6 $\log_{10}$ cfu.

To test the effect of D1–D4 (709–886) (SEQ ID NO: 6) on adhesion in vivo, the D1–D4 (709–886) (SEQ ID NO.6) polypeptide was added to the bacterial suspension to give a final concentration of 500 μg/ml prior to addition to the wound site. Thus, each wound site was dosed with 50 μg D1–D4 (709–886).

(iii) Evaluating Bacterial Adhesion/Colonisation in Vivo in the Presence of D1l4 D4 (709–886) Polypeptide At times e.g 1, 6, 24, 72, 168, 192 and 240 h post infection, one rat from each group was sacrificed using an i.p. injection of 0.5 ml Expiral. All cannulae were removed, rinsed in sterile PBS and each placed in 1 ml of fresh PBS (phosphate-buffered saline, 0.9%) and sonicated for 2 minutes in a sonicating water bath to remove adherent bacteria. Samples were plated out on to Mueller-Hinton agar to count the numbers of adherent, viable bacteria.

(iv) Results

D1–D4 (709–886) (SEQ ID NO. 6) polypeptide inhibits adhesion of *S. aureus* 8325-4 to cannulae during subcutaneous implantation in the rat. Of the cannulae removed after six hours implantation, three out of four were completely free of adherent organisms, and the number of organisms adherent to the fourth cannula was considerably less than the controls where no D1–D4 (709–886) (SEQ ID NO. 6) was added. Although some adherent bacteria were detected on cannulae after 8 days of implantation the numbers of organisms associated with D1–D4 (709–886) (SEQ ID NO. 6) treated cannulae (3.0±1.3 $\log_{10}$ cfu) was much lower than the untreated controls (5.4±1.4 $\log_{10}$ cfu). Considering the numbers of organisms used to infect the wound was $10^6$ this should exceed the numbers of contaminating organisms present in the operating theatre during surgery.

D1–D4 (709–886) (SEQ ID NO. 6) inhibited adhesion of *S. aureus* I20 (a virulent clinical isolate) for at least 10 days post infection. Cannulae were removed at 6, 24, 72, 168 and 240 h post infection and bacterial counts of between 4 and 6 $\log_{10}$ cfu were detectable for the duration of the study in the untreated cannulae. However, little or no bacterial numbers were detectable in the D1–D4 (709–886) (SEQ ID NO. 6) treated cannulae at any time.

Similar results were seen with two *S. epidermidis* strains. Despite an apparent delay in adherence of these strains, high numbers, between 5 and 6 $\log_{10}$ cfu were detectable at 10 days post infection on untreated cannulae. No bacteria were detectable on the D1–D4 (709–886) (SEQ ID NO. 6) treated cannulae at this time. Therefore, D1–D4 (709–886) (SEQ ID NO. 6) is potentially effective in blocking staphylococcal adhesion to indwelling medical devices when used prophylactically as a topical agent.

D. Effect of D1–D4 (709–838(P838T)) on Adhesion of Staphylococci (i) In Vitro Adhesion Assay Assay conditions were identical to those described for the evaluation of D1–D4 (709–886) (SEQ ID NO. 6) polypeptide in A.

(ii) Results

The D1–D4 (709–838(P838T)) (SEQ ID NO. 7) polypeptide was capable of inhibiting the adhesion of both *S. aureus* 8325-4 and *S. epidermidis* SE 902 to fibronectin-coated coverslips. The adhesion inhibition achieved with D1–D4 (709–838(P838T)) (SEQ ID NO. 7) was equivalent to that observed with D1–D4 (709–886) (SEQ ID NO. 6). In this study *S. aureus* 8325-4 adhesion was inhibited by 95% with 100 ng/ml polypeptide and *S. epidermidis* SE 902 adhesion inhibited by 85% at 100 μg/ml polypeptide.

(iii) In Vivo Adhesion Assay

Assay conditions were identical to those described for the evaluation of D1–D4 (709–886) (SEQ ID NO. 6) polypeptide in C.

(iv) Results

The D1–D4 (709–838(P838T)) (SEQ ID NO. 7) polypeptide was capable of inhibiting the adhesion of *S. aureus* I20 and *S. epidermidis* SE902 to vinyl cannulae during suncutaneous implantation in the rat. No adherent organisms were detected on cannulae treated with D1–D4 (709–838 (P838T)) (SEQ ID NO. 7) up to the 10 day time period studied in contrast to untreated controls where 4.5 $\log_{10}$ cfu were detected for *S. aureus* I20 and 6 $\log_{10}$ cfu for *S. epidermidis* SE 902.

TABLE 1

A Comparison of the DNA Encoding the Fibronectin Binding Domain
of S. aureus Fibronectin Binding Protein type A [SEQ ID NO:11]
and of the S. aureus J2385 DNA sequence [SEQ ID NO:5]

```
   1   GGCCAAAATAGCGGTAACCAGTCATTCGAGGAAGACACAGAAGAAGATAA    50    J2385
       ||||||||||||||||||||||||||||||||||||||||||||||+||
2350   GGCCAAAATAGCGGTAACCAGTCATTCGAGGAAGACACAGAAGAAGACAA  2399   Type A 51   ACCTAAATATGAACAAGGTGGCAATATCGTAGATATCGATTTCGATAGTG   100    J2385
       |||||||||||||||||||||||||||||||||||||||||+|||||||
2400   ACCTAAATATGAACAAGGTGGCAATATCGTAGATATCGATTTTGATAGTG  2449   Type A 101   TACCTCAAATTCATGGTCAAAATAAAGGTGATCAGTCATTCGAAGAAGAT   150    J2385
       |||||||||||||||||||||||||||||*|||||||||||||+||||||
2450   TACCTCAAATTCATGGTCAAAATAAAGGTAATCAGTCATTCGAGGAAGAT  2499   Type A 151   ACAGAGAAAGACAAGCCTAAATATGAACATGGTGGTAATATCATTGATAT   200    J2385
       |||||+|||||||||+|||||+||||||||||||+|||||+|||||||||
2500   ACAGAAAAAGACAAACCTAAGTATGAACATGGCGGTAACATCATTGATAT  2549   Type A 201   CGACTTCGACAGCGTGCCACATATTCATGGATTCAATAAGCACACTGAAA   250    J285
       ||||||||||||+|||||||||||||||||+|||||||||||||||||||
2550   CGACTTCGACAGTGTGCCACATATTCACGGATTCAATAAGCACACTGAAA  2599   Type A 251   TTATTGAAGAAGATACAAACAAAGATAAACCAAATTATCAATTCGGTGGA   300    J2385
       |||||||||||||||||||+|||||||||||||*|||||||||||||||||
2600   TTATTGAAGAAGATACAAATAAAGATAAACCAAGTTATCAATTCGGTGGA  2649   Type A 301   CACAATAGTGTTGACTTTGAAGAAGATACACTTCCACAAGTAAGTGGTCA   350    J2385
       |||||||||||||||||||||||||||||||||*|||||||+||+||
2650   CACAATAGTGTTGACTTTGAAGAAGATACACTTCCAAAAGTAAGCGGCCA  2699   Type A 351   TAATGAAGGTCAACAAACGATTGAAGAAGATACAAC............GC   388    J2385
       *||||||||||||||||||||||||||||||||||                ||
2700   AAATGAAGGTCAACAAACGATTGAAGAAGATACAACACCTCCAATCGTGC  2749   Type A 389   CGCCAACACCACCAACACCAGAAGTACCAAGTGAGCCGGAAACACCAACA   438    J2385
       |+|||||+|||||+||||||||||||||||||||||||||||||||||+
2750   CACCAACGCCACCGACACCAGAAGTACCAAGTGAGCCGGAAACACCAACG  2799   Type A 439   CCACCGACACCAGAAGTACCAAGTGAGCCGGAAACACCAACACCGCCAAC   488    J2385
       |||||+|||||||||||||||||||||||||||||||||||||+||+||
2800   CCACCAACACCAGAAGTACCAAGTGAGCCGGAAACACCAACACCACCGAC  2849   Type A 489   ACCAGAGGTACCAAGTGAGCCGGAAACACCAACACC                524    J2385
       ||||||+||+||+|||||||||+|||||+||||||||
2850   ACCAGAAGTGCCGAGTGAGCCAGAAACTCCAACACC                2885   Type A
```

+Silent Mutation
*Change of Amino Acid

TABLE 2

A comparison of the derived amino acid sequences of the
Fibronectin Binding Regions of the Fibronectin Binding
Proteins of Staphylococcus aureus (as published/Stapha
[SEQ ID NO:12] and Staphb [SEQ ID NO:13]) and
Staphylcoccus aureus J2385 [SEQ ID NO:10].
The Staphylococcus aureus sequence a comprises amino
acid residues 709–886 (as in Signas et al. loc. cit.)

```
         1 --> D1                              --> D2    50
J2385   GQNSGNQSFE EDTEEDKPKY EQGGNIVDID FDSVPQIHGQ NKGDQSFEED
Stapha  GQNSGNQSFE EDTEEDKPKY EQGGNIVDID FDSVPQIHGQ NKGNQSFEED
Staphb  GQNSGNQSFE EDTEEDKPKY EQGGNIVDID FDSVPQIHGQ NKGNQSFEED
```

TABLE 2-continued

A comparison of the derived amino acid sequences of the Fibronectin Binding Regions of the Fibronectin Binding Proteins of *Staphylococcus aureus* (as published/Stapha [SEQ ID NO:12] and Staphb [SEQ ID NO:13]) and *Staphylcoccus aureus* J2385 [SEQ ID NO:10]. The *Staphylococcus aureus* sequence a comprises amino acid residues 709—886 (as in Signas et al. loc. cit.)

```
          51                               --> D3                    100
J2385    TEKDKPKYEH GGNIIDIDFD SVPHIHGFNK HTEIIEEDTN KDKPNYQFGG
Stapha   TEKDKPKYEH GGNIIDIDFD SVPHIHGFNK HTEIIEEDTN KDKPSYQFGG
Staphb   TEKDKPKYEQ GGNIIDIDFD SVPHIHGFNK HTEIIEEDTN KDKPNYQFGG 101        --> D4                  --> WR1           146
J2385    HNSVDFEEDT LPQVSGHNEG QQTIEEDTT. ...PPTPPTP EVPSEPEPT
Stapha   HNSVDFEEDT LPKVSGQNEG QQTIEEDTTF PIVPPTPPTP EVPSEPETPT
Staphb   HNSVDFEEDT LPQVSGHNEG QQTIEEDTTF PIVPPTPPTP EVPSEPETPT 174
J2385    PPTPEVPSEP ETPTPPTPEV PSEPETPT
Stapha   PPTPEVPSEP ETPTPPTPEV PSEPETPT
Staphb   PPTPEVPSEP ETPTPPTPEV PTEP....
```

Figure

FIG. 1. is a diagrammatic representation of plasmid pBROC413. Bla indicates the ampicillin resistance gene, φ10 the T7 RNA polymerase promoter and rbs the ribosome binding site. Arrows for φ10 and bla give the direction of transcription. The polylinker site has been indicated. The plasmid is not drawn to scale and the size is approximate.

```
                    Sequence Listing-Key

SEQ ID NO:1      FIB 1

GGGAATTCAT  ATGGGCCAAA  ATAGCGGTAA  CCAGTC

SEQ ID NO:2      FIB 2

GCGGATCCTT  ACGTTGGTGG  CACGATTGGA  GGTG

SEQ ID NO:3      oligonucleotide (A)

CGGAATTCGT  CAACAAACGA  TTGAAGAAGA  TACAACGACG  TAAGATCTGG
ATCCGCATGC  GAATTCCG

SEQ ID NO:4      oligonucleotide (B)

CGGAATTCGT  CAACAAACGA  TTGAAGAAGA  TACAACGCCG  TAAGATCTGG
ATCCGCATGC  GAATTCCG

SEQ ID NO:5

GGCCAAAATA  GCGGTAACCA  GTCATTCGAG  GAAGACACAG  AAGAAGATAA
ACCTAAATAT  GAACAAGGTG  GCAATATCGT  AGATATCGAT  TTCGATAGTG
TACCTCAAAT  TCATGGTCAA  AATAAAGGTG  ATCAGTCATT  CGAAGAAGAT
ACAGAGAAAG  ACAAGCCTAA  ATATGAACAT  GGTGGTAATA  TCATTGATAT
CGACTTCGAC  AGCGTGCCAC  ATATTCATGG  ATTCAATAAG  CACACTGAAA
TTATTGAAGA  AGATACAAAC  AAAGATAAAC  CAAATTATCA  ATTCGGTGGA
CACAATAGTG  TTGACTTTGA  AGAAGATACA  CTTCCACAAG  TAAGTGGTCA
TAATGAAGGT  CAACAAACGA  TTGAAGAAGA  TACAACGCCG  CCAACACCAC
CAACACCAGA  AGTACCAAGT  GAGCCGGAAA  CACCAACACC  ACCGACACCA
GAAGTACCAA  GTGAGCCGGA  AACACCAACA  CCGCCAACAC  CAGAGGTACC
AAGTGAGCCG  GAAACACCAA  CACCTCCAAT  CGTGCCACCA  ACGTAA
```

Sequence Listing-Key

SEQ ID NO:6    D1-D4 (709-886)

GQNSGNQSFE EDTEEDKPKY EQGGNIVDID FDSVPQIHGQ NKGDQDFEED
TEKDKPKYEH GGNIIDIDFD SVPHIHGFNK HTEIIEEDTN KDKPNYQFGG
HNSVDFEEDT LPQVSGHNEG QQTIEEDTTP PTPPTPEVPS EPETPTPPTP
EVPSEPETPT PPTPEVPSEP ETPTPPIVPP T

SEQ ID NO:7    D1-D4 (709-838(P838T))(Example 7)

GQNSGNQSFE EDTEEDKPKY EQGGNIVDID FDSVPQIHGQ NKGDQSFEED
TEKDKPKYEH GGNIIDIDFD SVPHIHGFNK HTEIIEEDTN KDKPNYQFGG
HNSVDFEEDT LPQVSGHNEG QQTIEEDTTT

SEQ ID NO:8    D1-D4 (708-838)

GQNSGNQSFE EDTEEDKPKY EQGGNIVDID FDSVPQIHGQ NKGDQSFEED
TEKDKPKYEH GGNIIDIDFD SVPHIHGFNK HTEIIEEDTN KDKPNYQFGG
HNSVDFEEDT LPQVSGHNEG QQTIEEDTTP

SEQ ID NO:9    J2385 DNA (Table 1)

GGCCAAAATA GCGGTAACCA GTCATTCGAG GAAGACACAG AAGAAGATAA
ACCTAAATAT GAACAAGGTG GCAATATCGT AGATATCGAT TTCGATAGTG
TACCTCAAAT TCATGGTCAA AATAAAGGTG ATCAGTCATT CGAAGAAGAT
ACAGAGAAAG ACAAGCCTAA ATATGAACAT GGTGGTAATA TCATTGATAT
CGACTTCGAC AGCGTGCCAC ATATTCATGG ATTCAATAAG CACACTGAAA
TTATTGAAGA AGATACAAAC AAAGATAAAC CAAATTATCA ATTCGGTGGA
CACAATAGTG TTGACTTTGA AGAAGATACA CTTCCACAAG TAAGTGGTCA
TAATGAAGGT CAACAAACGA TTGAAGAAGA TACAACGCCG CCAACACCAC
CAACACCAGA AGTACCAAGT GAGCCGGAAA CACCAACACC ACCGACACCA
GAAGTACCAA GTGAGCCGGA AACACCAACA CCGCCAACAC CAGAGGTACC
AGGTGAGCCG GAAACACCAA CACC

SEQ ID NO:10    J2385 (Table 2)

GQNSGNQSFE EDTEEDKPKY EQGGNIVDID FDSVPQIHGQ NKGDQSFEED
TEKDKPKYEH GGNIIDIDFD SVPHIHGFNK HTEIIEEDTN KDKPNYQFGG
HNSVDFEEDT LPQVSGHNEG QQTIEEDTTP PTPPTPEVPS EPETPTPPTP
EVPSEPETPT PPTPEVPSEP ETPT

---

We claim:

1. An isolated D1–D4 polypeptide from a *Staphylococcus aureus* Fibronectin binding protein, wherein said polypeptide comprises an amino acid sequence selected from the group consisting of SEQ ID NO: 6, SEQ ID NO: 7, and SEQ ID NO: 8.

2. A polypeptide according to claim 1 consisting of a polypeptide selected form the group consisting of an amino acid sequence set forth in SEQ ID NO: 6, SEQ ID NO: 7, and SEQ ID NO: 8 optionally terminating in SEQ ID NO: 14 and optionally from one to five wall regions (WR) of *Staphylococcus aureus* Fibronectin binding protein in sequence.

3. A polypeptide according to claim 2 containing up to three wall regions.

4. A polypeptide according to claim 1 wherein the Fibronectin binding protein is from *S. aureus* J2385 encoded by the DNA sequence recited in SEQ ID NO: 5.

5. An isolated polypeptide comprising the amino acid sequence of SEQ ID NO:6.

6. A pharmaceutical composition comprising a polypeptide according to claim 1 and a pharmaceutically acceptable carrier.

* * * * *